United States Patent
Elke et al.

(10) Patent No.: US 10,172,869 B2
(45) Date of Patent: Jan. 8, 2019

(54) PROGESTERONE RECEPTOR MODULATORS FOR USE IN THE THERAPY OF UTERINE FIBROIDS

(71) Applicant: PregLem SA, Geneva (CH)

(72) Inventors: Bestel Elke, Saint-Julien-en-Genevois (FR); Osterloh Ian, Kent Bridge (GB); Loumaye Ernest, Cologny (CH); Dacquin Annie, Cranves Sales (FR); Jean Florence, Ferney Voltaire (FR)

(73) Assignee: PregLem SA, Geneva (CH)

( * ) Notice: Subject to any disclaimer, the term of this patent is extended or adjusted under 35 U.S.C. 154(b) by 0 days.

(21) Appl. No.: 14/781,759

(22) PCT Filed: Apr. 9, 2014

(86) PCT No.: PCT/IB2014/060558
§ 371 (c)(1),
(2) Date: Oct. 1, 2015

(87) PCT Pub. No.: WO2014/167510
PCT Pub. Date: Oct. 16, 2014

(65) Prior Publication Data
US 2016/0038510 A1 Feb. 11, 2016

(30) Foreign Application Priority Data

Apr. 10, 2013 (HU) ..................... 1300211

(51) Int. Cl.
*A61K 31/57* (2006.01)
*A61K 31/568* (2006.01)
*A61K 31/567* (2006.01)
*A61K 31/573* (2006.01)
*A61K 31/585* (2006.01)
*A61K 45/06* (2006.01)

(52) U.S. Cl.
CPC ............ *A61K 31/57* (2013.01); *A61K 31/567* (2013.01); *A61K 31/568* (2013.01); *A61K 31/573* (2013.01); *A61K 31/585* (2013.01); *A61K 45/06* (2013.01)

(58) Field of Classification Search
None
See application file for complete search history.

(56) References Cited

U.S. PATENT DOCUMENTS

| | | |
|---|---|---|
| 3,545,439 A | 12/1970 | Duncan |
| 3,920,805 A | 11/1975 | Roseman |
| 3,991,760 A | 11/1976 | Drobish et al. |
| 3,995,633 A | 12/1976 | Gougeon |
| 3,995,634 A | 12/1976 | Drobish |
| 4,012,496 A | 3/1977 | Schöpflin et al. |
| 4,155,991 A | 5/1979 | Schöpflin et al. |
| 4,250,611 A | 2/1981 | Wong |
| 4,286,587 A | 9/1981 | Wong |
| 4,292,965 A | 10/1981 | Nash et al. |
| 4,596,576 A | 6/1986 | de Nijs |
| 4,954,490 A | 9/1990 | Cook et al. |
| 5,073,548 A | 12/1991 | Cook et al. |
| 5,929,262 A | 7/1999 | Kim et al. |
| 5,972,372 A | 10/1999 | Saleh et al. |
| 2005/0208129 A1 | 9/2005 | Aiache et al. |
| 2005/0215536 A1 | 9/2005 | Chwalisz |

FOREIGN PATENT DOCUMENTS

| | | | |
|---|---|---|---|
| NL | 8500470 | 9/1986 | |
| WO | WO 95/00199 A1 | 1/1995 | |
| WO | WO 2004/065405 A1 | 8/2004 | |
| WO | WO 2004/078709 A2 | 9/2004 | |
| WO | WO 2005/097193 A1 | 10/2005 | |
| WO | WO 2006/010097 A2 | 1/2006 | |
| WO | WO 2009/095418 * | 8/2006 | ............ A61P 15/00 |
| WO | WO 2007/103510 A2 | 9/2007 | |
| WO | WO 2008/067086 A2 | 6/2008 | |
| WO | WO 2008/083192 A2 | 7/2008 | |
| WO | WO 2009/095418 A1 | 8/2009 | |

OTHER PUBLICATIONS

Benedetto et al (Expert Opin Drug Metab Toxicol 8:901-908, 2012) (Year: 2012).*
Apter, D., et al., "Clinical performance and endocrine profiles of contraceptive vaginal rings releasing 3-keto-desogestrel and ethinylestradiol," *Contraception* 42(3):285-295, Elsevier Inc., United States (1990).
Burton, F.G., et al., "Fabrication and testing of vaginal contraceptive devices designed for release of prespecified dose levels of steroids," *Contraception* 17(3):221-230, Elsevier Inc., United States (1978).
Burton, F.G., et al., "Low-level, progestogen-releasing vaginal contraceptive devices," *Contraception* 19(5):507-516, Elsevier Inc., United States (1979).
Donnez, J., et al., "Ulipristal acetate versus leuprolide acetate for uterine fibroids," *N Engl J Med*. 366(5):421-432, Massachusetts Medical Society, United States (2012).
Donnez, J., et al., "Ulipristal acetate versus placebo for fibroid treatment before surgery," *N Engl J Med*. 366(5):409-420, Massachusetts Medical Society, United States (2012).
Donnez, J. and Jadoul, P., "What are the implications of myomas on fertility? A need for a debate?" *Hum Reprod* 17(6):1424-1430, Oxford University Press, England (2002).

(Continued)

*Primary Examiner* — Craig D Ricci

(74) *Attorney, Agent, or Firm* — Sterne, Kessler, Goldstein & Fox P.L.L.C.

(57) ABSTRACT

The present invention relates to a long-term therapy including repeated treatment courses of ulipristal acetate or any metabolite thereof for treating uterine fibroids. The present invention also relates to a combined therapy applying ulipristal acetate with a progestin in order to improve the currently used treatment for uterine fibroids.

6 Claims, 4 Drawing Sheets

(56) References Cited

OTHER PUBLICATIONS

Figure 1:
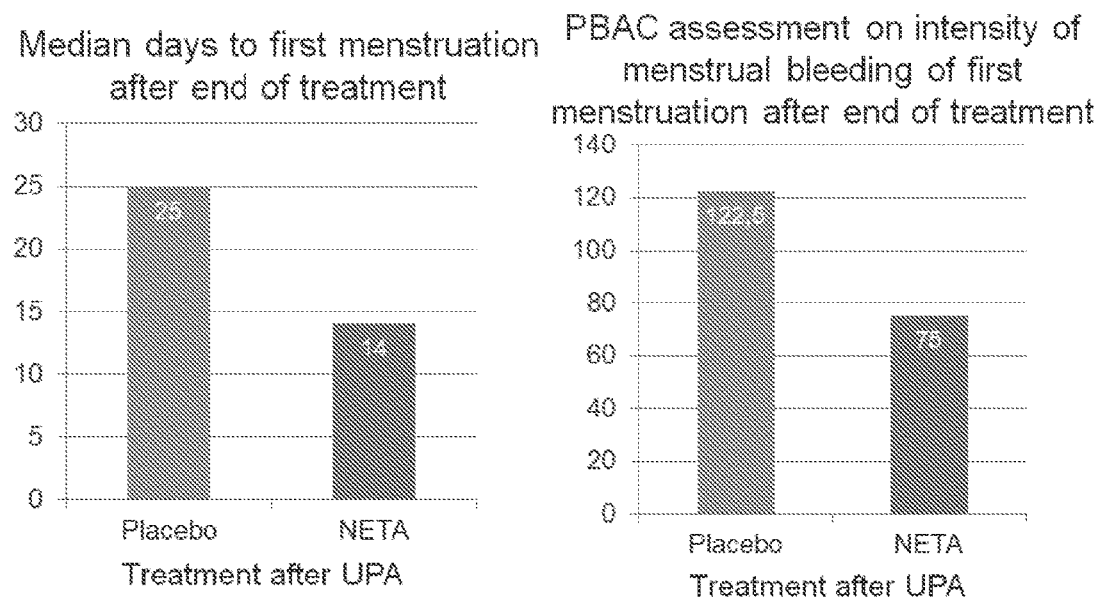

Eshre Capri Workshop Group, et al., "Endometrial bleeding," *Hum Reprod Update* 13(5):421-431, European Society of Human Reproduction and Embryology by Oxford University Press, England (2007).
Jackanicz, T.M., "Levonorgestrel and estradiol release from an improved contraceptive vaginal ring," *Contraception* 24(4):323-339, Elsevier Inc., United States (1981).
Kolankaya, A. and Arici, A., "Myomas and assisted reproductive technologies: when and how to act?" *Obstet Gynecol Clin North Am* 33(1):145-152, W.B. Saunders, United States (2006).
Langer, R., "New methods of drug delivery," *Science* 249(4976):1527-1533, American Association for the Advancement of Science, United States (1990).
Mutter, G.L., et al., "The spectrum of endometrial pathology induced by progesterone receptor modulators," *Mod Pathol.* 21(5):591-598, Nature Pub. Group, United States (2008).
Nieman, L.K., et al., "Efficacy and tolerability of CDB-2914 treatment for symptomatic uterine fibroids: a randomized, double-blind, placebo-controlled, phase IIb study," *Fertil Steril.* 95(2):767-772, Elsevier for the American Society for Reproductive Medicine, United States (2011).
Practice Committee of American Society for Reproductive Medicine in collaboration with Society of Reproductive Surgeons, "Myomas and reproductive function," *Fertil Steril* 90(5 Supplemental):S125-S130, Elsevier for the American Society for Reproductive Medicine, United States (2008).
Sitruk-Ware, R. and Small, M., "New methods of progestin delivery," *Contemp Clin Gynecol Obstet* 2:287-298, The Parthenon Publishing Group, United States (2002).
Sivin, I., et al., "A multicenter study of levonorgestrel-estradiol contraceptive vaginal rings. I-Use effectiveness. An international comparative trial," *Contraception* 24(4):341-358, Elsevier Inc., United States (1981).
Somigliana, E., et al., "Fibroids and female reproduction: a critical analysis of the evidence," *Hum Reprod Update* 13(5):465-476, European Society of Human Reproduction and Embryology by Oxford University Press, England (2007).
Timmer, C.J., et al., "Pharmacokinetics of 3-keto-desogestrel and ethinylestradiol released from different types of contraceptive vaginal rings," *Contraception* 42(6):629-642, Elsevier Inc., United States (1990).
Toivonen, J., "Intravaginal contraception with the synthetic progestin, R2010," *Contraception* 20(5):511-518, Elsevier Inc., United States (1979).
Victor, A., et al., "Peripheral plasma levels of d-norgestrel in women after oral administration of d-norgestrel and when using intravaginal rings impregnated with dl-norgestrel," *Contraception* 12(3):261-278, Elsevier Inc., United States (1975).
Wallach, E.E. and Vlahos, N.F., "Uterine myomas: an overview of development, clinical features, and management," *Obstet Gynecol.* 104(2):393-406, Lippincott Williams & Wilkins, United States (2004).
Weiner, E., et al., "New delivery systems for D-norgestrel," *Acta Obstet Gynecol Scand Suppl.* 54:35-43, Scandinavian Assn. of Obstetricians and Gynaecologists, Denmark (1976).
International Search Report for International Application No. PCT/IB2014/060558, European Patent Office, Netherlands, dated Nov. 11, 2014, 6 pages.
Attardi, B.J., et al., "In vitro antiprogestational/antiglucocorticoid activity and progestin and glucocorticoid receptor binding of the putative metabolites and synthetic derivatives of CDB-2914, CDB-4124, and mifepristone," *J Steroid Biochem Mol Biol* 88(3):277-288, Pergamon, England (2004).
Blithe, D.L., et al., "Development of the selective progesterone receptor modulator CDB-2914 for clinical indications" *Steroids* 68(10-13):1013-1017, Elsevier Inc., United States (2003).
Cramer, S.F. and Patel, A., "The Frequency of Uterine Leiomyomas," *Am J Clin Pathol* 94(4):435-438, American Society of Clinical Pathologists, United States (1990).
Melis, G.B., et al., "Pharmacokinetic evaluation of ulipristal acetate for uterine leiomyoma treatment," *Expert Opin Drug Metab Toxicol* 8(7):901-908, Informa Healthcare, England (2012).

\* cited by examiner

|  | UPA + Placebo |  |  |
|---|---|---|---|
|  | Adequate Specimen Consensus | | |
|  | Screening | One menstrual cycle after 1st UPA Course | One menstrual cycle after 4th UPA Course |
| Benign Endometrium | 56 (100%) | 65 (100%) | 47 (100%) |
| Hyperplasia | 0 | 0 | 0 |
| Polyps (benign) | 0 | 2 (3.1%) | 1 (2.1%) |

Figure 7.

|  | UPA + Placebo | | |
|---|---|---|---|
|  | Screening | One menstrual cycle after 1st UPA Course | One menstrual cycle after 4th UPA Course |
| PAEC | 4 (7.1%) | 20 (30.8%) | 11 (23.4%) |
| *Epithelial changes* | *4 (7.1%)* | *19 (29.2%)* | *9 (19.1%)* |
| *Extensive cyst formation* | *0* | *9 (13.8%)* | *3 (6.4%)* |
| *Unusual vascular changes* | *0* | *5 (7.7%)* | *5 (10.6%)* |

Figure 8.

PROGESTERONE RECEPTOR MODULATORS FOR USE IN THE THERAPY OF UTERINE FIBROIDS

TECHNICAL FIELD

The present invention relates to efficient long-term therapy including periodically repeated treatment courses for treating uterine fibroids. The present invention also relates to a combined therapy in order to improve the currently used treatment for uterine fibroids.

BACKGROUND OF THE INVENTION

Patients suffering from uterine fibroids require intervention in order to improve the diseases' symptoms.

Uterine fibroids, which also called leiomyomata are common pelvic fibroid tumors occurring in up to 20% of women over 30 years of age. Leiomyomata represent one of the most frequent indications of surgical procedures in woman of reproductive age. Studies show that up to 77% of women have microscopic or macroscopic uterine fibroids at the time of menopause (Cramer et al, 1990). Leiomyomata may be 1 mm to 20 cm in diameter. Usually, treatment choice is guided by the patient's age and desire to preserve fertility and/or her uterus.

Most fibroids are asymptomatic but nearly half of women with fibroids have significant and often disabling symptoms including menorrhagia, pelvic pain, dysmenorrhea and pressure effects. In addition, fibroids that distort the uterine cavity can have adverse effects on fertility (American Society for Reproductive Medicine. Myomas and reproductive function. Fertil Steril 2008; 90:S125-S130 and Somigliana E, Vercellini P, Daguati R, et al. Fibroids and female reproduction: a critical analysis of the evidence. Hum Reprod Update 2007; 13:465-76 and Kolankaya A, Arici A. Myomas and assisted reproductive technologies: when and how to act? Obstet Gynecol Clin North Am 2006; 33:145-52 and Donnez J, Jadoul P. What are the implications of myomas on fertility? A need for a debate? Hum Reprod 2002; 17:1424-30.).

In such women, heavy uterine bleeding is a leading reason for medical consultation, surgery and work days lost (Collins J, Crosignani P G. Endometrial bleeding. Hum Reprod Update 2007; 13:421-31).

Over the last few years a variety of non-invasive treatments has become available to women with symptomatic fibroids and provides alternatives to the surgery.

Among others the use of anti-progestational agents before a surgical treatment has also been proposed to shrink uterine leiomoymata (WO2007/103510) or to render the patient amenorrheic. More specifically, WO2007/103510 relates to the treatment of uterine fibrosis using effective low doses of anti-progestational agent and length of treatment is shorter than previously thought possible.

A number selective progesterone receptor modulators (SPRMs) are under development for the treatment of gynecological diseases such as uterine fibroid, endometriosis, adenomyosis, abnormal uterine bleeding and dysfunctional uterine bleeding.

SPRMs such as ulipristal acetate (UPA) offer a unique potential clinical application in gynecology because effectively controls excessive bleeding, abdominal pain and size of myoma due to uterine fibroids and consequently improve the quality of life of the patients.

WO2008/083192 relates to formulations for improving the bioavailability of ulipristal acetate as one of the anti-progestins can be advantageously used inter alia to antagonize endogenous progesterone. Ulipristal acetate is cited as a possible antiprogestin among a large number of other relevant compounds. This patent application also provides a long list of disorders which might be treated by the claimed composition. Uterine fibroids is cited as one possible disease to cure among others. In the application use of UPA for the treatment of uterine fibroids is not explored explicitly and no examples are described in order to support the feasibility of treatment.

WO2009/095418 relates to a method for treating uterine fibroids, which method comprises administering to a patient in need thereof an effective amount of ulipristal acetate or any metabolite thereof. The inventors have shown that a low dosage, e.g. a daily dosage of 5 to 15 mg, preferably 10 mg, ulipristal acetate was the most effective. Ulipristal acetate or any metabolite thereof is particularly efficient to reduce or stop bleeding in a patient afflicted with uterine fibroids, or to reduce the size of uterine fibroids. The patient may be administered with an oral dosage of ulipristal acetate or any metabolite thereof during a period of about 2 to about 4 months.

In the prior art there was a strong technical prejudice against the long-term and repeated administration of SPRM's, for example asoprisnil, mifepristone or ulipristal acetate may induces progesterone-receptor modulator-associated endometial changes, which can be considered as harmful side effects (Mutter G. L., Mod. Path. (2008), 1-8; Nieman, L. K., Fertility and Sterility (2011) 95, 2, 767-772.)

Accordingly, UPA have been effective for the treatment of uterine fibroids, but the administration of UPA was limited to a period no longer than about 2 to about 4 months, preferably 3 months and widely accepted by skilled person.

Although treatments for about 2 to about 4 months exist, there remain significant unmet needs for improvement of uterine fibroid therapy.

SUMMARY OF THE INVENTION

The present invention provides new treatment method in the field of uterine fibroid therapy. We have surprisingly found that the technical prejudice against the long-term and repeated administration of SPRM's with special regards to UPA was not well-established. Results gained from the clinical study have proven beyond any doubt that the administration of adequate dosage of ulipristal acetate or of a metabolite thereof for the treatment of uterine fibroids can be repeated. The long-term repeated administration provides a number of great benefits. For example reduction of uterine bleeding (higher percentage of subjects in amenorrhea), decrease in volume of myomas, reduction in patent-reported pain, etc. were demonstrated. At the same time the frequency of PAEC (Progesteron receptor modulator-Associated Endometrial Changes) was independent of length of treatment.

Accordingly, in one aspect the invention provides a method for the treatment of uterine fibroids comprising administering ulipristal acetate or any metabolite thereof in a therapeutically effective amount, wherein said ulipristal acetate or any metabolite thereof is to be administered in subsequent treatment periods and a treatment period lasts 2-6 months and each treatment period is followed by a drug-free period.

We have also investigated the possible repeated use of a new method of combined treatment where the treatment course of UPA limited to three months known from the state of the art was followed by the administration of a progestin, especially NETA for a period of 5-30 days and an additional drug-free period. In this way additional benefits of this combined treatment have been proven, namely earlier and more predictable resumption of menstruations and reduction of intensity of menstruation especially after the first treatment course of UPA.

So, in the second aspect the invention relates to a method for the treatment of uterine fibroids comprising administering therapeutically effective amount of ulipristal acetate or any metabolites thereof in combination with a therapeutically effective amount of a progestin, wherein said ulipristal acetate or any metabolite thereof is to be administered in subsequent treatment period of 2-6 months and progestin is to be administered for a subsequent treatment period of 5-30 days.

It also means that even if the administration of NETA takes place following UPA course limited to the period of about 2 to about 6 months the above-mentioned benefits resulted in the combined treatment are obtained.

Accordingly, in the third aspect the invention also relates to a method for the treatment of uterine fibroids comprising administering therapeutically effective amount of ulipristal acetate or any metabolites thereof in combination with a therapeutically effective amount of a progestin, wherein said compounds are to be administered in a repetitive manner comprising the followings:
a, administering ulipristal acetate;
b, thereafter administering progestin;
c, thereafter a drug-free period.

DETAILED DESCRIPTION OF THE INVENTION

The present invention relates to ulipristal acetate or any metabolites thereof for use in the treatment of uterine fibroids comprising administering ulipristal acetate or any metabolites thereof in a therapeutically effective amount, wherein said ulipristal acetate or any metabolite thereof is to be administered in subsequent treatment periods and a treatment period lasts 2-6 months and each treatment period is followed by a drug-free period.

In a preferred embodiment the invention relates to ulipristal acetate or any metabolites thereof for use in the treatment of uterine fibroids comprising administering ulipristal acetate or any metabolite thereof, wherein a treatment period lasts 2-4 months.

In a still preferred embodiment the invention relates to ulipristal acetate or any metabolites thereof for use in treatment of uterine fibroids comprising administering ulipristal acetate or any metabolite thereof, wherein a treatment period lasts 12 weeks.

In a more preferred embodiment the invention relates to ulipristal acetate or any metabolites thereof for use in treatment of uterine fibroids comprising administering ulipristal acetate or any metabolite thereof, wherein a drug-free period comprises at least one menstruation cycle.

In a further embodiment the invention relates to ulipristal acetate or any metabolites thereof for use in treatment of uterine fibroids comprising administering ulipristal acetate or any metabolite thereof, wherein a drug-free period comprises at least two menstruation cycles.

In an other embodiment the invention relates to ulipristal acetate or any metabolites thereof for use in treatment of uterine fibroids comprising administering ulipristal acetate or any metabolite thereof, wherein a drug-free period comprises at least three menstruation cycles.

In an other preferred embodiment the invention relates to ulipristal acetate or any metabolites thereof for use in treatment of uterine fibroids comprising administering ulipristal acetate or any metabolite thereof, wherein a drug-free period is not more than 6 months.

In a more preferred embodiment the invention relates to ulipristal acetate or any metabolites thereof for use in treatment of uterine fibroids comprising administering ulipristal acetate or any metabolite thereof, wherein said ulipristal acetate or any metabolite thereof is to be administered daily.

In a still more preferred embodiment the invention relates to ulipristal acetate or any metabolites thereof for use in treatment of uterine fibroids comprising administering ulipristal acetate or any metabolite thereof, wherein ulipristal acetate or any metabolite thereof is to be administered in a daily amount of 5-15 mg.

In a most preferred embodiment the invention relates to ulipristal acetate or any metabolites thereof for use in treatment of uterine fibroids comprising administering ulipristal acetate, wherein ulipristal acetate is to be administered in a daily amount of 10 mg.

The invention relates to ulipristal acetate or any metabolite thereof in combination with a progestin for use in the treatment of uterine fibroids wherein ulipristal acetate or any metabolite thereof is to be administered for a treatment period of 2-6 months and progestin is to be administered for a subsequent treatment period of 5-30 days.

The invention also relates to ulipristal acetate or any metabolite thereof in combination with a progestin for use in the treatment of uterine fibroids wherein said compounds are to be administered in a repetitive manner comprising the followings:
a, administering ulipristal acetate;
b, thereafter administering progestin;
c, thereafter a drug-free period.

In a preferred embodiment the invention relates to ulipristal acetate or any metabolite thereof in combination with a progestin for use in the treatment of uterine fibroids wherein progestin is selected from the group comprising derivatives of 19-nortestosterone, derivatives of 17α-acetoxyprogesterone, levonorgestrel and dospirenone.

In a still preferred embodiment the invention relates to ulipristal acetate or any metabolite thereof in combination with a progestin for use in the treatment of uterine fibroids wherein progestin is norethisterone acetate.

In a more preferred embodiment the invention relates to ulipristal acetate or any metabolite thereof in combination with a progestin for use in the treatment of uterine fibroids wherein norethisterone acetate is to be administered in a daily amount of 5-15 mg.

In a further embodiment the invention relates to ulipristal acetate or any metabolite thereof in combination with a progestin for use in the treatment of uterine fibroids wherein norethisterone acetate is to be administered in a daily amount of 10 mg.

In an other embodiment the invention relates to ulipristal acetate or any metabolite thereof in combination with a progestin for use in the treatment of uterine fibroids wherein ulipristal acetate or any metabolite thereof is to be administered in a daily amount of 5-15 mg.

In an other preferred embodiment the invention relates to ulipristal acetate in combination with a progestin for use in the treatment of uterine fibroids wherein ulipristal acetate is to be administered in a daily amount of 10 mg.

In a more preferred embodiment the invention relates to ulipristal acetate or any metabolite thereof in combination with a progestin for use in the treatment of uterine fibroids wherein ulipristal acetate or any metabolite thereof is to be administered for a treatment period of 2-4 months.

In a still more preferred embodiment the invention relates to ulipristal acetate or any metabolite thereof in combination with a progestin for use in the treatment of uterine fibroids wherein ulipristal acetate or any metabolite thereof is to be administered for a treatment period of 12 weeks.

In a most preferred embodiment the invention relates to ulipristal acetate or any metabolite thereof in combination with a progestin for use in the treatment of uterine fibroids wherein progestin is to be administered for a treatment period of 10 days.

In a still preferred embodiment the invention relates to ulipristal acetate in combination with a progestin for use in the treatment of uterine fibroids wherein ulipristal acetate is to be administered for a treatment period of 12 weeks and norethisterone acetate is to be administered for a treatment period of 10 days.

In a further preferred embodiment the invention relates to ulipristal acetate or any metabolite thereof in combination with a progestin for use in the treatment of uterine fibroids wherein a drug-free period comprises at least one menstruation cycle.

In a preferred embodiment the invention relates to ulipristal acetate or any metabolite thereof in combination with a progestin for use in the treatment of uterine fibroids wherein a drug-free period comprises at least two menstruation cycles.

In a most preferred embodiment the invention relates to ulipristal acetate or any metabolite thereof in combination with a progestin for use in the treatment of uterine fibroids wherein a drug-free period comprises at least three menstruation cycles.

The present invention relates to a method for the treatment of uterine fibroids comprising administering ulipristal acetate or any metabolites thereof in a therapeutically effective amount, wherein said ulipristal acetate or any metabolite thereof is to be administered in subsequent treatment periods and a treatment period lasts 2-6 months and each treatment period is followed by a drug-free period.

In a preferred embodiment the invention relates to a method for the treatment of uterine fibroids comprising administering ulipristal acetate or any metabolite thereof, wherein a treatment period lasts 2-4 months.

In a still preferred embodiment the invention relates to a method for the treatment of uterine fibroids comprising administering ulipristal acetate or any metabolite thereof, wherein a treatment period lasts 12 weeks.

In a more preferred embodiment the invention relates to a method for the treatment of uterine fibroids comprising administering ulipristal acetate or any metabolite thereof, wherein a drug-free period comprises at least one menstruation cycle.

In a further embodiment the invention relates to a method for the treatment of uterine fibroids comprising administering ulipristal acetate or any metabolite thereof, wherein a drug-free period comprises at least two menstruation cycles.

In an other embodiment the invention relates to a method for the treatment of uterine fibroids comprising administering ulipristal acetate or any metabolite thereof, wherein a drug-free period comprises at least three menstruation cycles.

In an other preferred embodiment the invention relates to a method for the treatment of uterine fibroids comprising administering ulipristal acetate or any metabolite thereof, wherein a drug-free period is not more than 6 months.

In a more preferred embodiment the invention relates to a method for the treatment of uterine fibroids comprising administering ulipristal acetate or any metabolite thereof, wherein said ulipristal acetate or any metabolite thereof is to be administered daily.

In a still more preferred embodiment the invention relates to a method for the treatment of uterine fibroids comprising administering ulipristal acetate or any metabolite thereof, wherein ulipristal acetate or any metabolite thereof is to be administered in a daily amount of 5-15 mg.

In a most preferred embodiment the invention relates to a method for the treatment of uterine fibroids comprising administering ulipristal acetate, wherein ulipristal acetate is to be administered in a daily amount of 10 mg.

The present invention relates to a method for the treatment of uterine fibroids comprising administering therapeutically effective amount of ulipristal acetate or any metabolites thereof in combination with a therapeutically effective amount of a progestin, wherein said ulipristal acetate or any metabolite thereof is to be administered in subsequent treatment period of 2-6 months and progestin is to be administered for a subsequent treatment period of 5-30 days.

The present invention also relates to a method for the treatment of uterine fibroids comprising administering therapeutically effective amount of ulipristal acetate or any metabolites thereof in combination with a therapeutically effective amount of a progestin, wherein said compounds are to be administered in a repetitive manner comprising the followings:

a, administering ulipristal acetate;
b, thereafter administering progestin;
c, thereafter a drug-free period.

In a preferred embodiment the invention relates to a method for the treatment of uterine fibroids comprising administering ulipristal acetate or any metabolites thereof in combination with a progestin, wherein progestin is selected from the group comprising derivatives of 19-nortestosterone, derivatives of 17α-acetoxyprogesterone, levonorgestrel and dospirenone.

In a more preferred embodiment the invention relates to a method for the treatment of uterine fibroids comprising administering ulipristal acetate or any metabolites thereof in combination with a progestin, wherein progestin is norethisterone acetate.

In a still preferred embodiment the invention relates to a method for the treatment of uterine fibroids comprising administering ulipristal acetate or any metabolites thereof in combination with a progestin, wherein norethisterone acetate is to be administered in a daily amount of 5-20 mg.

In a still more preferred embodiment the invention relates to a method for the treatment of uterine fibroids comprising administering ulipristal acetate or any metabolites thereof in combination with a progestin, wherein norethisterone acetate is to be administered in a daily amount of 10 mg.

In a further preferred embodiment the invention relates to a method for the treatment of uterine fibroids comprising administering ulipristal acetate or any metabolites thereof in combination with a progestin, wherein ulipristal acetate is to be administered in a daily amount of 5-15 mg.

In an other preferred embodiment the invention relates to a method for the treatment of uterine fibroids comprising administering ulipristal acetate or any metabolites thereof in combination with a progestin, wherein ulipristal acetate is to be administered in a daily amount of 10 mg.

In a still preferred embodiment the invention relates to a method for the treatment of uterine fibroids comprising administering ulipristal acetate or any metabolites thereof in combination with a progestin, wherein ulipristal acetate or any metabolites thereof is to be administered for a treatment period of 2-4 months.

In a further preferred embodiment the invention relates to a method for the treatment of uterine fibroids comprising administering ulipristal acetate or any metabolites thereof in combination with a progestin, wherein ulipristal acetate or any metabolites thereof is to be administered for a treatment period of 12 weeks.

In an other preferred embodiment the invention relates to a method for the treatment of uterine fibroids comprising administering ulipristal acetate or any metabolites thereof in combination with a progestin, wherein progestin is to be administered for a treatment period of 10 days.

In a further preferred embodiment the invention relates to a method for the treatment of uterine fibroids comprising administering ulipristal acetate or any metabolites thereof in combination with a progestin, wherein ulipristal acetate or any metabolites thereof is to be administered for a treatment period of 12 weeks and norethisterone acetate is to be administered for a treatment period of 10 days.

In a further preferred embodiment the invention relates to a method for the treatment of uterine fibroids comprising administering ulipristal acetate or any metabolites thereof in combination with a progestin, wherein a drug-free period comprises at least one menstruation cycle.

In a further preferred embodiment the invention relates to a method for the treatment of uterine fibroids comprising administering ulipristal acetate or any metabolites thereof in combination with a progestin, wherein a drug-free period comprises at least two menstruation cycles.

In a further preferred embodiment the invention relates to a method for the treatment of uterine fibroids comprising administering ulipristal acetate or any metabolites thereof in combination with a progestin, wherein a drug-free period comprises at least three menstruation cycles.

As used herein "administering" refers to contact of a therapeutically effective amount of ulipristal acetate or any metabolites thereof, to the subject.

Usually, the "subject" is well-recognized in the art, and is used herein to refer to a mammal and more preferably to a human being, and even more preferably to a human female.

Uterine fibroids are benign non-cancerous tumors that originate from the smooth muscle layer, the myometrium and the accompanying connective tissue of the uterus. Uterine fibroid are also known as myoma, uterine hypertrophy, uterine leiomyomata, leiomyoma, myoma, fibromyoma, leiofibromyoma, fibroleiomyoma, fibroma, myometrial hypertrophy, fibrosis uteri, and fibrotic metritis. Fibroids are the most common benign tumors in females with a prevalence of 20-40% in women of reproductive age (Wallach E E, Vlahos N F. "Uterine myomas: an overview of development, clinical features, and management". Obstet Gynecol (2004), 104, 393-406).

As used herein "treatment" or "treating" refers to at least an amelioration (or reduction) and/or preventing the symptoms associated with uterine fibroids. Amelioration and/or prevention are used in a broad sense to refer to at least a reduction in the magnitude of a parameter, e.g. symptom. As such, treatment also includes situations where the pathological condition, or at least symptoms associated therewith, are completely or partially inhibited, e.g. prevented from happening, or stopped, e.g. terminated, such that the host no longer suffers from the condition, or at least the symptoms that characterize the condition.

As used herein "therapeutically effective amount" refers to a dosage sufficient to show an effective response as described above.

As used herein "menstrual cycle" refers to the term for the physiological changes that occur in fertile women and other female primates for the purposes of sexual reproduction. Human menstrual cycle, a "monthly" cycle that can vary around an average of around 28 days per cycle.

The chemical formula of ulipritral acetate, also known as CDB-2914, is 17α-acetoxy-11β[4-N,N-dimethylamino-phenyl)-19-norpregna-4,9-diene-3,20-dione. It is a well-known steroid, more specifically a 19-norprogesterone, which possesses antiprogestational and antiglucocorticoidal activity. This compound, and methods for its preparation, are described in U.S. Pat. Nos. 4,954,490, 5,073,548, and 5,929,262, and international patent applications WO2004/065405 and WO2004/078709. Properties of this compound are further described in Blithe et al, 2003.

An "active metabolite", as used herein, refers to a product produced through metabolism in the body of a specified compound, in the present case ulipristal acetate, or salt thereof and which exhibits the same biological activity as the ulipristal acetate. Such metabolites may result for example from the oxidation, reduction, hydrolysis, amidation, deamidation, esterification, deesterification, enzymatic cleavage, and the like, of the administered ulipristal acetate, or of a salt thereof.

Active metabolites of ulipristal acetate, or of a salt thereof, may be identified using routine techniques known in the art and their activities determined using tests such as those described herein. Such metabolites may result for example from the oxidation, reduction, hydrolysis, amidation, deamidation, esterification, deesterification, enzymatic cleavage, and the like, of the administered ulipristal acetate or of a salt thereof. Accordingly, the invention includes active metabolites of ulipristal or of a salt thereof, including compounds produced by a process comprising contacting a compound of this invention with a mammal for a period of time sufficient to yield a metabolic product thereof. Such metabolite may also be produced in vitro by oxidation, reduction, hydrolysis, amidation, deamidation, esterification, deesterification, or enzymatic cleavage of the corresponding ulipristal acetate or salt thereof. Examples of metabolites of ulipristal acetate (CDB-2914), include those described in Attardi et al, 2004, e.g. monodemethylated CDB-2914 (CDB-3877); didemethylated CDB-2914 (CDB-3963); 17α-hydroxy CDB-2914 (CDB-3236); aromatic A-ring derivative of CDB-2914 (CDB-4183).

As used herein, a "progesterone agonist" or "progestin" refers to a compound or agent that activates the progesterone receptor. The progestin is selected from the group comprising derivatives of 19-nortestosterone, derivatives of 17α-acetoxyprogesterone (pregnanes), levonorgestrel and dospirenone. Preferably, the progestin is norethindrone (norethisterone) acetate (NETA).

For a brief review of present methods for drug delivery, see, Langer, Science 249:1527-1533 (1990), which is incorporated herein by reference. Methods for preparing administrable compounds are known or are apparent to those skilled in the art and are described in more detail in, for example, Remington's Pharmaceutical Science, 17th Ed., Mack Publishing Company, Easton, Pa. (1985), which is incorporated herein by reference.

The mode of administration possibilities include solid compositions such as tablets, capsules, lozenges, pills, transdermal patches, dental pastes, suppositories, inhalants, solutions, ointments, parenteral depots, vaginal rings, vaginal gels and intra-uterine delivery systems.

For solid compositions, conventional nontoxic solid carriers may be used which include, for example, pharmaceutical grades of mannitol, lactose, starch, magnesium stearate, sodium saccharine, talcum, cellulose, glucose, sucrose. For oral administration, a pharmaceutically acceptable nontoxic composition is formed by incorporating any of the normally employed excipients, such as those carriers previously listed.

Oral solid dosage forms are preferentially compressed tablets or capsules. Compressed tablets may contain diluents to increase the bulk of the progesterone receptor modulator, the SPRM, or a metabolite thereof, so that production of a compressed tablet of practical size is possible. Binders, which are agents which impart cohesive qualities to powdered materials may be also necessary. Povidone, starch, gelatin, sugars such as lactose or dextrose, and natural and synthetic gums may be used. Disintegrants are generally necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion of the tablet material to surfaces in the manufacturing process and to improve the flow characteristics of the powder material during manufacture. Colloidal silicon dioxide is most commonly used as a glidant and compounds such as talc, magnesium stearate or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of the progestogen agent or progesterone receptor modulator and inert ingredients. Procedures for production and manufacture of hard gelatin and soft elastic capsules are well known in the art (See Remington).

The oral route is preferred. Other routes of administration can be suitable in comparison with oral routes using blood levels to provide clinical success.

Buccal forms or devices are also useful, such as those described in U.S. patent application 20050208129, herein incorporated by reference. U.S. patent application 20050208129 describes a prolonged release bioadhesive mucosal therapeutic system containing at least one active principle, with an active principle dissolution test of more than 70% over 8 hours and to a method for its preparation. Said bioadhesive therapeutic system comprises quantities of natural proteins representing at least 50% by weight of active principle and at least 20% by weight of said tablet, between 10% and 20% of a hydrophilic polymer, and compression excipients, and comprising between 4% and 10% of an alkali metal alkylsulphate to reinforce the local availability of active principle and between 0.1% and 1% of a monohydrate sugar.

For parenteral administration, fluid unit dosage forms are prepared utilizing the compounds and a sterile vehicle, water being preferred. Ulipristal acetate or a metabolite thereof, depending on the vehicle and concentration used, can be either suspended or dissolved in the vehicle. In preparing solutions the compound can be dissolved in water for injection and filtered sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compounds are suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of ulipristal.

Additionally, a suppository can be employed to deliver ulipristal. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These suppositories can weigh from about 1 to 2.5 gm.

Transdermal delivery systems comprising a penetration enhancer and an occlusive backing are of use to deliver ulipristal or a metabolite thereof. Examples of penetration enhancers include dimethyl sulfoxide, dimethyl acetamide and dimethylformamide.

Systems comprising polymeric devices which slowly release or slowly erode and release within the body to provide continuous supplies of ulipristal are also of use. Suitable delivery systems include subcutaneous devices or implants such as those routinely used to deliver norgestrienone or progestin R2323 and other medicaments.

In some embodiments of the present invention, the pharmaceutical compositions suitable for vaginal and/or intra-uterine administration are in the form of intravaginal or vaginal rings. These rings are annularly shaped articles made of inert elastomeric materials that can be introduced into the vagina in a simple manner without medical assistance. The ring fits between the rear wall of the vagina and the upper edge of the pubic bone. Numerous types of vaginal rings have been described in the patent and non-patent literature alike. See, e.g., U.S. Pat. Nos. 4,012,496 and 4,155,991 (both to Schopflin et al.); U.S. Pat. No. 4,292,965 (Nash) (which teaches three-layered rings); U.S. Pat. No. 3,545,439 (Duncan); U.S. Pat. No. 3,920,805 (Roseman); U.S. Pat. Nos. 3,991,760 and 3,995,634 (both to Drobish et al.); U.S. Pat. No. 3,995,633 (Gougeon); U.S. Pat. Nos. 4,250,611 and 4,286,587 (both to Wong); U.S. Pat. No. 4,596,576 (de Nijs); WO95/00199 (Lehtinen et al.); NL 8500-470-A; and Apter, et al., Contraception 42:285-295 (1990); Burton, et al., Contraception 27:221-230 (1978); Burton et al., Contraception 19:507-516 (1979); Jackanicz, Contraception 24:323-339 (1981); Sivin, et al., Contraception 24:341-358 (1981); Timmer, et al., Contraception 43:629-642 (1990); Toivonen, Contraception 20:511-518 (1979); and Sitruk Ware, et al., Contemporary Clin. Gynecol. & Obstet. 2:287-98 (2002).

Many basic ring designs are known in the art, e.g., the homogeneous ring, two-layered rings, the Roseman ring and three-layered rings. See, e.g., Weiner et al., Acta Obstet Gynecol. Scand, Suppl. 54, 1977 p. 35; U.S. Pat. No. 3,920,805 to Roseman and U.S. Pat. No. 4,012,496 to Schopflen. U.S. Pat. No. 3,545,439 to Duncan and Victor, et al., Contraception 12:261, 1975. U.S. Pat. No. 4,012,496 to Schoepflin, et al., U.S. Pat. No. 5,972,372. Vaginal rings for use in the present invention can be those described in WO2006/010097.

Suitable material providing sustained release of the active ingredient from the vaginal ring comprises for example silicone, ethylene vinyl acetate (EVA) or polyurethane (PU). Preferred material is EVA or PU.

The pharmaceutical compositions suitable for vaginal and/or intrauterine administration of the present invention may also take the form of a non-vaginal ring sustained release composition, e.g., gels, foams and suppositories (e.g, effervescent suppositories) that will provide a sustained release of the PRM, SPRM, or active metabolite thereof. Each of these suitable pharmaceutical compositions will contain at least one pharmaceutically acceptable excipient, carrier or diluent. Persons skilled in the art may select appropriate ones to make the various types of sustained-release compositions e.g., by resort to standard texts in the art.

In cases where the progesterone receptor modulator, a SPRM, or a metabolite thereof, is included in a solution, the formulation may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others.

Useful intranasal formulations of a progesterone receptor modulator, a SPRM, or a metabolite thereof may contain at least one stabilizer and/or one surfactant. Among the pharmaceutically acceptable surfactants are polyoxyethylene castor oil derivatives, such as polyoxyethylene-glycerol-triricinoleate, also known as polyoxyl 35 caster oil (CREMOPHOR EL), or poloxyl 40 hydrogenated castor oil (CREMOPHOR RH40) both available from BASF Corp.; mono-fatty acid esters of polyoxyethylene (20) sorbitan, such as polyoxyethylene (20) sorbitan monolaurate (TWEEN 80), polyoxyethylene monostearate (TWEEN 60), polyoxyethylene (20) sorbitan monopalmitate (TWEEN 40), or polyoxyethylene 20 sorbitan monolaurate (TWEEN 20) (all available from ICI Surfactants of Wilmington, Del.); polyglyceryl esters, such as polyglyceryl oleate; and polyoxyethylated kernel oil (LABRAFIL, available from Gattefosse Corp.). Preferably, the surfactant will be between about 0.01% and 10% by weight of the pharmaceutical composition. Among the pharmaceutically useful stabilizers are antioxidants such as sodium sulfite, sodium metabisulfite, sodium thiosulfate, sodium formaldehyde sulfoxylate, sulfur dioxide, ascorbic acid, isoascorbic acid, thioglycerol, thioglycolic acid, cysteine hydrochloride, acetyl cysteine, ascorbyl palmitate, hydroquinone, propyl gallate, nordihydroguaiaretic acid, butylated hydroxytoluene, butylated hydroxyanisole, alpha-tocopherol and lecithin. Preferably, the stabilizer will be between about 0.01% and 5% by weight of the pharmaceutical composition.

Suspensions may also include chelating agents such as ethylene diamine tetraacetic acid, its derivatives and salts thereof, dihydroxyethyl glycine, citric acid and tartaric acid among others. Additionally, proper fluidity of a suspension can be maintained, for example, by the use of coating materials such as lecithin, by the maintenance of the required particle size in the case of dispersions and by the use of surfactants, such as those previously mentioned. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay; and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Preferably, ulipristal acetate, is orally administered in a therapeutically daily effective amount of 5 to 15 mg, preferably 5 to 12 mg, more preferably 8 to 10 mg, even more preferably 10 mg.

When ulipristal acetate or a metabolite thereof is administered in combination with a progestin, in particular with NETA, the therapeutically daily effective amount of the progestin is 5 to 20 mg, preferably 5 to 15 mg, more preferably 8 to 10 mg, even more preferably 10 mg.

The administration period is from 5 days up to 30 days, preferably from 8 days up to 15 days, more preferably 10 days.

As used herein, the term "long-term" administration means in relation to the expression therapy for treatment of uterine fibroids refers to a period of approximately 6 months or longer.

The present invention also contemplates a kit for a long-term treatment comprising the SPRM or any metabolite thereof, optionally with progestins and/or instructions for use.

Generally, the Kit comprises a container and a label or package insert on or associated with the container. Suitable containers include, for example, bottles, vials, syringes, etc. The containers may be formed from a variety of materials such as glass or plastic. The container holds the progesterone receptor modulator, or any metabolite thereof of the invention which is effective for normalizing menstrual bleeding on the long-term in a subject suffering from a benign gynecological disease. The label or package insert indicates that the composition is used for treating the condition of the invention.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

LIST OF FIGURES

Figure 2:
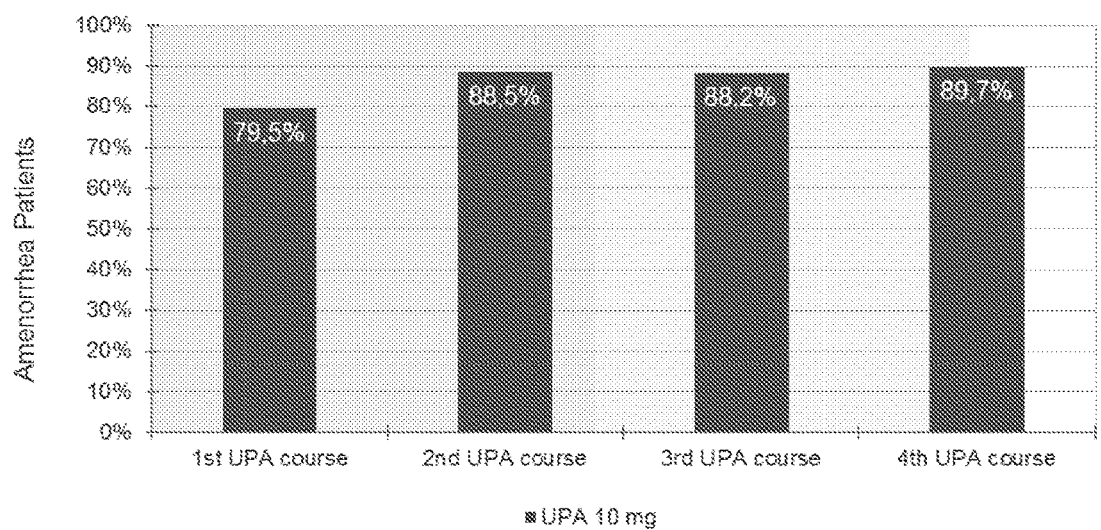
Figure 3:
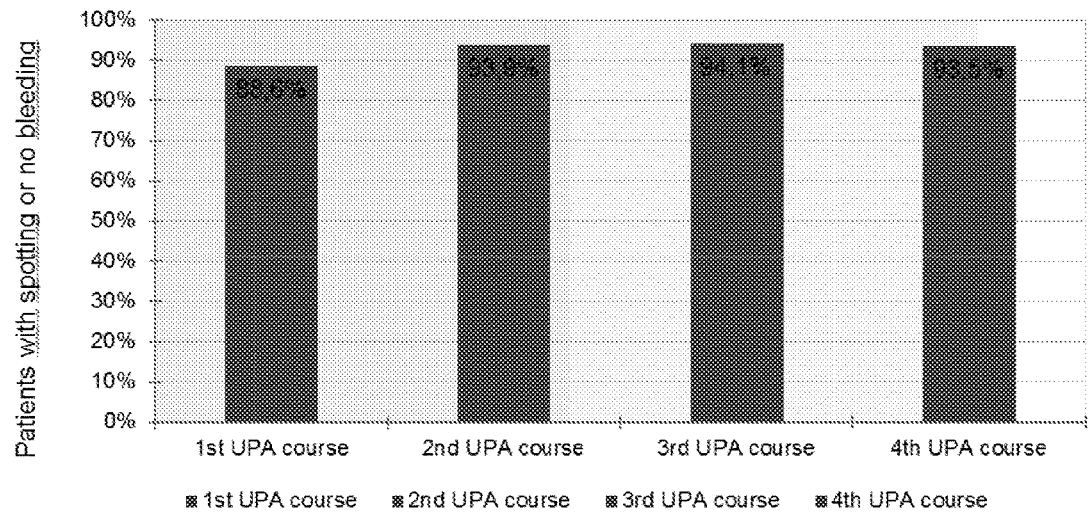

FIG. 1: Median return to menstruation following end of UPA treatment and PBAC assessment on intensity of menstrual bleeding of first menstruation after end of treatment FIG. 2: Percentage of subjects in amenorrhea at the end of each treatment courses FIG. 3: Percentage of subjects with spotting or no bleeding at the end of each treatment courses FIG. 4: Median percent change showing efficacy of fibroid volume reduction after UPA treatment FIG. 5: Median return to menstruation following end of UPA treatment FIG. 6: Median PBAC assessment on intensity of menstrual bleeding of first menstruation after end of treatment FIG. 7: Endometrial histology (benign endometrium, hyperplasia, polyps) after UPA treatment FIG. 8: Endometrial histology (PAEC) after UPA treatment

EXAMPLES

Example 1

Multicenter, Phase III Study to Investigate the Efficacy and Safety of 3-Months of Treatment with UPA Followed by 10 Days of Treatment with NETA or Placebo All patients received a 3-month treatment course of UPA 10 mg once-daily followed by randomized oral NETA 10 mg once-daily or matching placebo for 10 days. UPA treatment was started during the first 4 days of menstruation. NETA or placebo was taken daily for the first 10 days following the cessation of UPA. The schedule incorporated the potential for women to enter an extension study involving repeated intermittent courses of UPA 10 mg.

Parameters Assessed

In the clinical trial the effect of treatment of uterine fibroids have been assessed by means of parameters such as uterine bleeding using the pictorial blood-loss assessment chart (PBAC), condition of the uterus using transvaginal ultrasound (TVUS) and endometrial biopsy, endometrial histology using endometrial biopsy and pain using the Short-Form McGill Pain Questionnaire (SF-MPQ and quality of life using the Uterine Fibroid Symptom and Health-Related Quality of Life (UFS-QoL) questionnaire.

The efficacy end points were: percentage of amenorrheic patients at the end of UPA treatment; change from baseline in the volume of the three largest myomas to end of UPA treatment and 2 weeks after menstruation following end of NETA/placebo treatment; and change from baseline in pain and QoL to end of UPA treatment.

The safety endpoints included the number and proportion of patients experiencing treatment-emergent adverse events (TEAEs), including clinically significant changes in vital signs, physical examination, gynecological or breast examination, electrocardiogram (ECG), ovarian ultrasound, changes from baseline in endometrial thickness and clinically significant changes in endometrium biopsy. Other safety endpoints were change from baseline in hematology, coagulation, biochemistry, lipids, adrenocorticotropic hormone (ACTH), thyroid stimulating hormone (TSH) and prolactin, as well as serum levels of estradiol (E2).

Exploratory endpoints included assessment of the strength of the first menstruation after UPA treatment (using PBAC), time to return of menstruation following treatment end, and frequency of post-treatment PAEC observed in the endometrial biopsy after return of menstruation.

Results

Efficacy Endpoints

Amenorrhea

At the end of UPA treatment, 164 women (78.5%) were amenorrheic (95% CI, 72.4 to 83.5%). The mean and median time from first day of menstruation on, or just prior to, first dose of UPA to amenorrhea were 10.6 and 5.0 days respectively, with a range of 2 to 60 days. From day 10 until end of treatment <5% of patients on any particular day reported any bleeding, and <2% reported heavy bleeding.

Fibroid Volume

The median change in the combined volume of the largest three fibroids between baseline and end of UPA treatment was −45.1% (interquartile range [IQR], −66.1 to −24.9%). This decrease was maintained after UPA treatment and return of menstruation (median change, −45.8%; IQR, −63.3 to −13.0%). In 74.7% of the women there was a ≥25% reduction in the volume of the three largest fibroids.

Pain Relief and Quality of Life

An improvement in pain was recorded with median change from baseline scores at Weeks 5, 9 and end of UPA treatment of −5.0 (IQR, −12.0 to −1.0), −6.0 (IQR, −14.0 to −1.6) and −6.0 (IQR, −14.0 to −2.0) respectively. Similarly, pain assessed by the VAS showed a decrease (improvement) in score, from a median baseline level of 38 (IQR, 17 to 63). Median change was −21 (IQR, −39 to −2), −26 (IQR, −54 to −7) and −25 (IQR, −54 to −6) at Weeks 5, 9 and at end of UPA treatment respectively. Patients had moderately severe symptoms and moderately impaired QoL at baseline. After UPA treatment, women showed an improvement in QoL, defined by a median change from baseline score of −34.4 (IQR, −46.9 to −21.9) for symptom severity and a median increase of 28.5 (IQR, 11.6 to 44.0) for the health-related QoL (HRQL) total score compared to baseline.

Safety Endpoints

Three serious adverse events (SAEs) were reported for two patients during the study. All occurred post-treatment and were considered not related to study medication. One subject was hospitalized due to two episodes of excessive uterine bleeding 28 days after completion of double-blind treatment. The other subject had right lobular breast cancer and was withdrawn from the study.

During UPA treatment, 318 TEAEs occurred in 120 women (57.4%), with 3.8% classified as severe. One hundred and twelve TEAEs in 62 women (29.7%) were considered to be UPA related. No SAE occurred during the UPA treatment phase. Only one TEAE (continuous headache of moderate intensity) led to treatment withdrawal. TEAEs occurring in >3% of women were headache (16.3%), nasopharyngitis (6.7%), hot flushes (4.8%), fatigue (4.3%), breast discomfort/tenderness (3.8%), pelvic pain (3.8%), vertigo (3.8%), nausea (3.8%) and lower abdominal pain (3.3%).

In the double-blind treatment phase 18 events were reported by 11 women (11.2%) in the NETA group and two events by two women (1.9%) in the placebo group. In the post-treatment phase, TEAEs were reported in 26.5% and 27.2% of women in the NETA and placebo groups respectively.

During UPA treatment, E2 levels were generally at mid-follicular phase levels. The mean E2 level was 149.9 pg/mL (median, 120.0 pg/mL) at screening and at Visit 5 the mean E2 level was 81.6 pg/mL (median, 55.0 pg/mL). No significant changes in ACTH, TSH, or prolactin were recorded. A small number of patients had a marginal increase in hepatic transaminases which all resolved during continued treatment and/or by the time of the follow-up visit.

Exploratory Endpoints

Menstrual Bleeding

Median return to menstruation following end of UPA treatment was 14.0 days (range, 2 to 42 days) for the NETA treatment group compared to 25 days in those receiving placebo (range, 1 to 62 days) (p≤0.001). (FIG. 1)

The overall total median change in PBAC score of the first menstruation following treatment completion compared to that at baseline was −91.5 (IQR, −220 to 23), with a median baseline score of 216. The median change in PBAC score for the NETA treatment group was −122 (IQR, −229 to −9) compared to −69 (IQR, −167 to 40) for the placebo group (p=0.012). (FIG. 1)

Endometrial Histology Following Double-Blind Treatment

Endometrial histology was benign in all cases. The percentage of non-physiological endometrial features was higher after UPA treatment than at screening (10.9% at screening vs. 25.6% after UPA treatment) with no significant difference between NETA and placebo groups (28.3% in the placebo group and 22.6% in the NETA group). However, after NETA treatment extensive cyst formation (one of the features of PAEC) was less frequent compared to placebo (2.4% in the NETA group vs. 12.0% in the placebo group).

The biopsy 12 weeks after UPA treatment confirmed benign endometrial histology in all biopsies (n=38); one benign endometrial polyp was reported in the NETA group. At this time in this subgroup, there was no case of PAEC in the NETA group and only one case in the placebo group which comprised epithelial changes and extensive cystic formation.

Endometrial Thickness

There was a small increase in the percentage of women with endometrial thickness >16 mm by the end of UPA treatment (9.1% vs. 1.5% at screening). Results for the double-blind treatment groups show small increases after NETA (3.5% vs. 0% at screening) and placebo (9.5% vs. 3.0% at screening). Endometrial thickness was comparably influenced by NETA and placebo. Three months later, none of the patients assessed had a thickness >16 mm.

Example 2

Long-Term Extension of a Multicenter, Phase III Study to Investigate the Efficacy and Safety of 3-Months of Treatment with UPA Followed by 10 Days of Treatment with NETA or Placebo in Subjects with Myomas and Heavy Uterine Bleeding The study consisted of three periods of 3 months open-label UPA treatment, each followed by 10 days of double-blind treatment with NETA or placebo and then a drug-free period. Subjects were randomly assigned to a NETA or matching placebo arm with a 1:1 ratio.

In study described in Example 1, 251 subjects were screened at 21 sites and 209 subjects started treatment with UPA of which 202 attended the end of UPA treatment visit. Of those that completed study of Example 1 (190 subjects), 132 subjects from 19 sites opted to continue in to the extension study.

In the study of Example 1 and for each present study courses, UPA 10 mg was orally administered once daily for a period of 90 days, followed by 10 mg NETA or matching placebo once daily for a period of 10 days. The first treatment course in the present study consisted of 90 days UPA 10 mg treatment followed by 10 days of double-blind treatment (same as in Example 1 study) started between the first and fourth day of menstruation (inclusive) following visit after the end of treatment, or one month later if uterine sparing surgery had been performed and myomas were still present. The second and third treatment courses of the present study started on the first day of menstruation following visits after ends of each treatment courses, respectively.

Parameters Assessed

Parameters assessed are the same as it was described in Example 1.

Results

Efficacy Endpoints

Amenorrhea

The study demonstrated that intermittent courses of UPA 10 mg daily oral treatment for 3 months were effective in the reduction of uterine bleeding, although there was evidence that the effectiveness of 1st treatment course was lower than for 2nd-4th courses. Of the 132 subjects in the ITT Population, the percentage of subjects in amenorrhea at the end of 1, 2, 3 and 4 treatment courses were 79.5%, 88.5%, 88.2% and 89.7%, respectively (see FIG. 2), and the mean (median) time to amenorrhea (time from the first dose of UPA in each treatment course to the start of amenorrhea) was 9.4 days (4.0 days), 3.3 days (2.0 days), 5.3 days (3.0 days) and 4.2 days (3.0 days), respectively. Over days 9-90, more than 9 days of any level of bleeding (heavy bleeding, bleeding or spotting) were reported by 21 (15.9%), 8 (6.3%), 4 (3.4%) and 4 (3.9%) subjects (ITT Population) (see FIG. 3). The results for the individual placebo and NETA treatment groups were relatively similar.

Fibroid Volume

Figure 4:
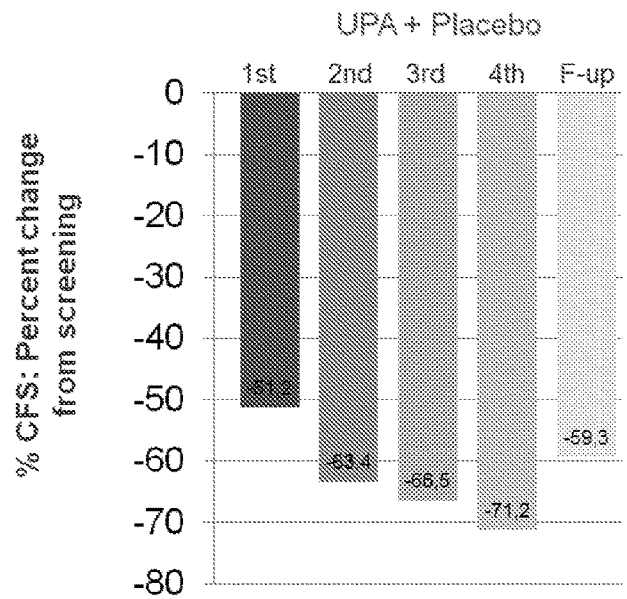

The total volume of the 3 largest myomas identified at screening was shown to decrease following each treatment course, with a maximum decrease seen at the end of 4th treatment course when a mean (median) percent change from screening of −53.53% (−72.08%) was observed. This decrease was maintained, although reduced, up to the follow-up visit (approximately 2 weeks after the third menstruation following 4th treatment course), when a mean (median) percent change from screening of −33.68% (−58.84%) was reported (FIG. 4). The uterine volume measured by US also decreased during the study and similarly maintained after end of treatment, even so due to the focused mechanism of action of ulipristal acetate, the reduction was less than seen for the volume reduction of the 3 largest myomas.

Pain Relief and Quality of Life

The reduction in uterine bleeding and volume of the myomas was accompanied by a reduction in patient-reported pain, as measured by the Short-Form McGill Pain Questionnaire (SF-MPQ); the 3 SF-MPQ Parts demonstrated improvement from baseline at all visits. The results were similar for the placebo and NETA treatment groups, as for the overall treatment group. Quality of life was measured using the specific Uterine Fibroid Symptom and Health-Related Quality of Life (UFS-QoL) symptom severity and health-related QoL (HRQL) scales, and also by the general EuroQoL-5 Dimensions (EQ-5D) questionnaire. In the UFS-QoL the average symptom severity score showed an improvement (decrease) from baseline, there was also an improvement (increase) on average for the HRQL total score compared to baseline. In the ED-5D questionnaire the most common problems reported at baseline and throughout the study were in the pain/discomfort and anxiety/depression dimensions, and for both of these measures improvement was sustained throughout the study.

Figure 5:
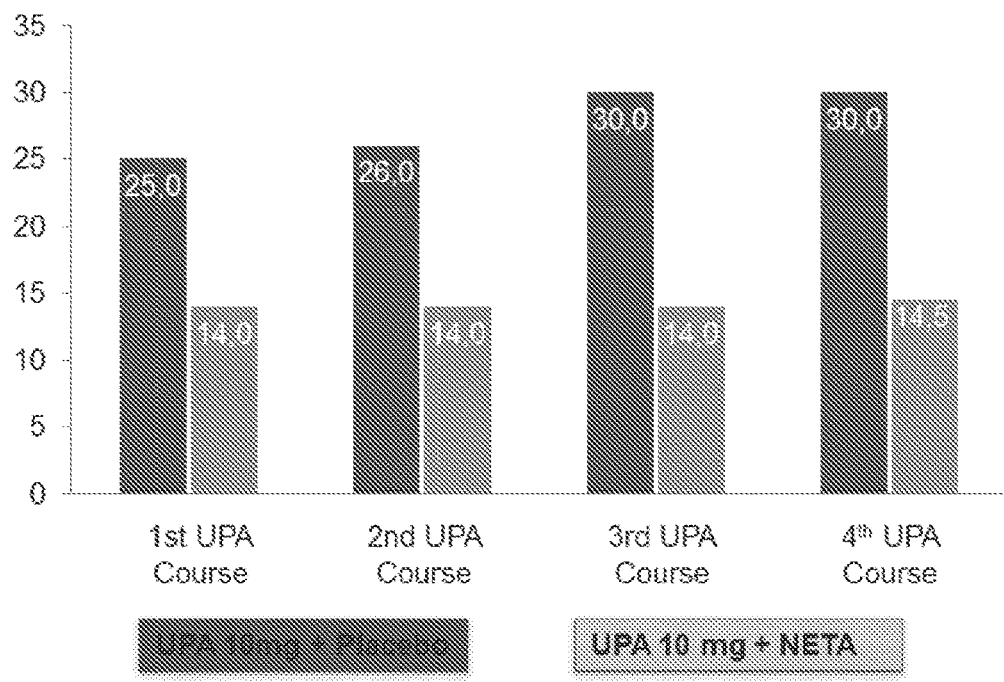
Figure 6:
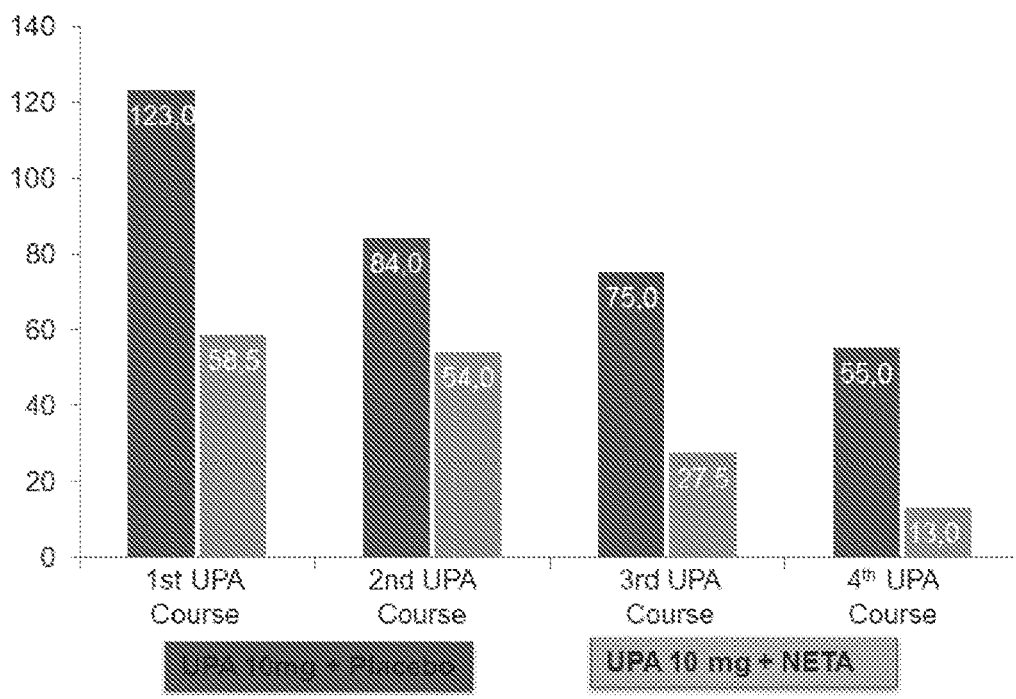

Following the end of each treatment course al but 4 subjects with available data returned to menstruation. As anticipated, median times to return of menstruation following discontinuation of UPA 1-4 treatment courses were significantly shorter for subjects from the NETA group compared to those from the placebo group (p<0.001) (FIG. 5). In addition, the heaviness of bleeding as measured by the PBAC score (days 1-8), was greater in subjects from the placebo group after each treatment course. Bleeding for both groups appeared to decrease after each subsequent treatment course, although this was most noticeable in subjects from the NETA group (FIG. 6).

One demonstration of the efficacy, safety and acceptability of UPA treatment in this patient population is the change in surgery undertaken at the end of the study compared to that initially planned. At the start of study of Example 1, surgery was planned for 66 (50%) of the 132 subjects in the ITT population, but by the end of present study surgery was not performed for 125 (94.7%) subjects; only 7 subjects underwent surgery.

Safety Endpoints

Safety assessments including vital signs, laboratory and endocrine measurements, as well as reported treatment-emergent adverse events (TEAEs) and Serious Adverse Event (SAEs) demonstrated that this intermittent repeated administration schedule is well tolerated and did not lead to the identification of any new safety concerns. As might be expected, the number of TEAEs reported during the first UPA treatment course, was greater than seen in subsequent treatment courses, no increase in frequency for any TEAE could be observed. Overall, few TEAEs were reported during double-blind treatment; the addition of NETA 10 mg for 10 day after each treatment course of UPA did not raise any safety concerns.

As reported in previous studies, following treatment with a single treatment course of 3 months UPA, an increase in endometrium thickness was observed. However, the increase in endometrium thickness were monitored after each treatment courses and endometrium thickness data for the 2 treatment groups were compared. Thickness data for subjects from the placebo group were higher compared to those for the NETA group, and more subjects from the placebo group had endometrium thickness >16 mm at each of these visits.

Endometrium biopsy samples were evaluated by 3 independent pathologists. All biopsy samples had a diagnosis of benign endometrium by consensus review (FIG. 7). Observations of non-physiological changes in endometrium biopsy samples suggested that the incidence was highest in samples taken following first treatment course and second treatment course, including epithelial changes, unusual vascular changes and extensive cyst formation (FIG. 8). At the follow-up visit, the non-physiological changes were similar to observations seen at screening, suggesting rapid reversal of changes once treatment had ended.

The invention claimed is:

1. A method of treating uterine fibroids in a patient in need thereof, the method comprising administering to the patient ulipristal acetate or a metabolite thereof in a therapeutically effective amount in two sequential treatment periods,
   wherein the ulipritsal acetate or a metabolite thereof is administered daily in an amount of from 5 to 15 mg,
   wherein each treatment period lasts 12 weeks and each treatment period is followed by a drug-free period which lasts about one menstruation cycle, and
   wherein the first treatment period starts from the first day of menstruation to the fourth day of menstruation, and the second treatment period starts on the first day of menstruation after the end of the drug-free period.

2. The method of claim 1, wherein the daily amount is 10 mg ulipristal acetate.

3. The method of claim 1, wherein the patient is a human female.

4. The method of claim 1, wherein the administering results in benign endometrium histology of the patient.

5. The method of claim 1, wherein the administering results in increased median return to menstruation time of the patient.

6. The method of claim 1, wherein the administering results in an endometrial thickness of the patient of no greater than 16 mm.

* * * * *

UNITED STATES PATENT AND TRADEMARK OFFICE
CERTIFICATE OF CORRECTION

PATENT NO. : 10,172,869 B2
APPLICATION NO. : 14/781759
DATED : January 8, 2019
INVENTOR(S) : Bestel et al.

Page 1 of 1

It is certified that error appears in the above-identified patent and that said Letters Patent is hereby corrected as shown below:

On the Title Page

Item (12), delete "Elke et al." and insert -- Bestel et al. --

Item (72), delete "Bestel Elke" and insert -- Elke Bestel --

Item (72), delete "Osterloh Ian" and insert -- Ian Osterloh --

Item (72), delete "Loumaye Ernest" and insert -- Ernest Loumaye --

Item (72), delete "Dacquin Annie" and insert -- Annie Dacquin --

Item (72), delete "Jean Florence" and insert -- Florence Jean --

In the Claims

Column 18, Line 17, Claim 1, delete "ulipritsal" and insert -- ulipristal --

Signed and Sealed this
Twenty-eighth Day of April, 2020

Andrei Iancu
*Director of the United States Patent and Trademark Office*